(12) United States Patent
Hendricksen

(10) Patent No.: US 6,398,712 B1
(45) Date of Patent: Jun. 4, 2002

(54) ERGONOMIC STEERING WHEEL SYSTEM

(76) Inventor: Mark W. Hendricksen, 10805 E. 22nd Ave., Spokane, WA (US) 99206

( * ) Notice: Subject to any disclaimer, the term of this patent is extended or adjusted under 35 U.S.C. 154(b) by 0 days.

(21) Appl. No.: 09/495,811

(22) Filed: Feb. 1, 2000

(51) Int. Cl.[7] .............................. A61N 2/00; G05G 1/10
(52) U.S. Cl. ............................................ 600/9; 74/558
(58) Field of Search .............................. 600/9, 14, 15; 340/407, 579; 361/143; 5/693; 341/20; 345/156; 244/165

(56) References Cited

U.S. PATENT DOCUMENTS

| | | | |
|---|---|---|---|
| 3,337,776 A | * 8/1967 | Elmi | .......................... 361/143 |
| 4,059,830 A | * 11/1977 | Threadgill | .................. 340/579 |
| 4,134,395 A | 1/1979 | Davis | |
| 4,602,359 A | 7/1986 | Palmer | |
| 4,622,952 A | 11/1986 | Gordon | |
| 4,622,953 A | 11/1986 | Gordon | |
| 5,161,272 A | 11/1992 | Yamaguchi et al. | |
| 5,304,111 A | 4/1994 | Mitsuno et al. | |
| 5,312,321 A | 5/1994 | Holcomb | |
| 5,441,495 A | 8/1995 | Liboff et al. | |
| 5,782,743 A | 7/1998 | Russell | |
| 5,788,624 A | 8/1998 | Lu et al. | |
| 5,817,000 A | 10/1998 | Souder | |
| 5,842,966 A | 12/1998 | Markoll | |
| 5,871,438 A | 2/1999 | Adizzone | |
| 6,236,306 B1 | * 5/2001 | Liebelt | ........................ 340/407 |

OTHER PUBLICATIONS

Stephan Barrett, M.D.; The "Reflexology Steering Wheel"; Sep. 16, 1997; Quackwatch Home Page.*

* cited by examiner

*Primary Examiner*—Eric F. Winakur
*Assistant Examiner*—Nikita R Veniaminov

(57) ABSTRACT

Disclosed is a therapeutic and comfort system for operators of motor vehicles which imparts a magnetic and/or electric field, or therapeutic waves, on or around the steering wheel of a vehicle.

24 Claims, 3 Drawing Sheets

ERGONOMIC STEERING WHEEL SYSTEM

TECHNICAL FIELD

This invention pertains to a system which provides an ergonomic magnet steering wheel used for its therapeutic, blood circulation or health care effect on the operator of the vehicle. The creation of a wave field, such as a magnetic field and/or an electric field, will provide vehicle operators with a therapeutic or health care effect in their fingers, hands and/or wrists as they grip the steering wheel.

BACKGROUND OF THE INVENTION

The potentially therapeutic, healing, preventative, health effect and biological effects of the application of numerous types and magnitudes of magnetic and/or electromagnetic fields have been studied and are the subject of numerous prior patents, such as U.S. Pat. Nos. 5,084,003, 3,921,620, 5,002,068 (each of which are incorporated herein by reference). Exposing part or all of the human body to certain magnetic fields is believed to alleviate pain, increase the circulation of the blood in the area in which the magnetic field (for instance) is imposed, in addition to other benefits.

Although many have experienced the adverse effects, the adverse blood circulation effects of holding on to a steering wheel for prolonged periods of time has not been heretofore adequately remedied or alleviated.

Despite the long felt need, there has not heretofore been an adequate system for alleviating the symptoms of holding a steering wheel, especially for long haul truckers, cross country drivers, and others who spend a substantial amount of time driving. The automotive industry has likewise not heretofore experienced the use of a magnet to produce a magnetic field with a potential health effect, at an area above and around the steering wheel of a vehicle.

Wearing magnetic or magnetized gloves or handwear is not practical as the vehicle operator needs to handle and interface with components and things which may sensitive to a magnetic field. Further, gloves or handwear are not desirable to many drivers.

There has been a long felt, but heretofore unsatisfied need for such a magnetic therapeutic system, and this invention satisfies this need with the advantages and features described herein.

BRIEF DESCRIPTION OF THE DRAWINGS

Preferred embodiments of the invention are described below with reference to the accompanying drawings, which are briefly described below.

DETAILED DESCRIPTION OF THE PREFERRED EMBODIMENTS

Figure 1:
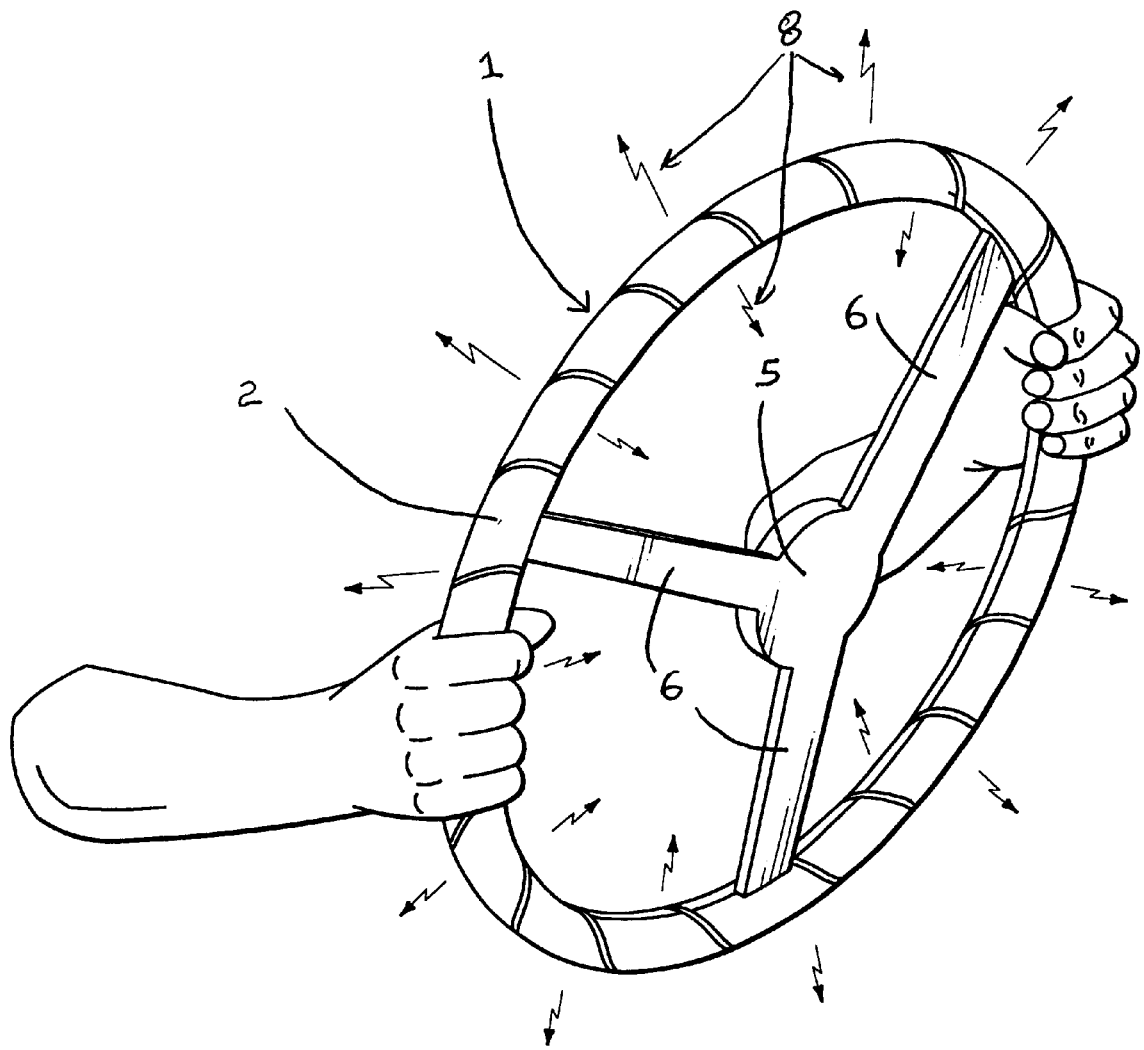
FIG. 1 is a perspective view of one embodiment of an ergonomic steering wheel as contemplated by this invention, illustrating a wave field around the steering wheel.

Many of the fastening, connection, manufacturing and other means and components utilized in this invention are widely known and used in the field of the invention described, their exact nature or type is not necessary for an understanding and use of the invention by a person skilled in the art or science, and they will not therefor be discussed in significant detail. Furthermore, the various components shown or described herein for any specific application of this invention can be varied or altered as anticipated by this invention and the practice of a specific application of any element may already be widely known or used in the art or by persons skilled in the art or science and each will not therefor be discussed in significant detail.

The terms "a", "an" and "the" as used in the claims herein, are used in conformance with longstanding claim drafting practice and not in a limiting way. Unless specifically set forth herein, the terms "a", "an" and "the" are not limited to one of such, but instead mean "at least one".

The term "one or more magnets" as used herein is intended to be interpreted broadly to include magnetic material used or intended to be used to impart a magnetic field at a position where the operator's hands and/or wrists will be placed during operation. The magnetic field may be positioned for any one of numerous reasons, including without limitation, for therapeutic, preventative, health care, comforting, productivity and/or biological effects.

The terms magnet and magnetic material may include any type or kind of magnet or magnetic material with no one in particular being required to practice this invention. By way of providing some, but not an exhaustive list of examples, this may include without limitation, permanent magnets, magnetic materials which create a changing magnetic field, ferromagnetic components, and others. The magnets or magnetic material may be fluxing, fixed, moving or otherwise, within the contemplation of this invention, and may create pulsed, changing, fluxing, modulating, and/or fixed/constant magnetic, waved or energy fields (as a few examples) within the contemplation of this invention. They may including alternating poles, north poles, south poles, or combinations thereof, and different shapes of the magnets and magnetic fields, all within the same magnet or magnetic layer, within the contemplation of this invention.

Examples of potentially ergonomic or therapeutic magnetic sheets are set forth in U.S. Pat. Nos. 5,304,111, 5,871,438 and 5,32,321, which are each hereby incorporated herein by this reference.

While the term steering wheel is used herein and reference is made to motor vehicles, it applies equally to the control wheel in an airplane and the steering wheel in a boat, tractor, etc., which is how that term should be interpreted herein.

The term steering wheel cover as used herein includes partial and entire covers to be applied on or over part or all of a steering wheel or vehicle steering apparatus.

The term magnetic shield as used herein is any device, shield, material or mechanism which provides, without limitation, an offset, insulation, isolation or other shielding of the magnetic fields produced. This may include a magnetic isolating shield, a magnetic isolating body, a ferrous or other special material for magnetic shielding. No particular shape or type of shielding is required to practice this invention.

Magnetic shielding may be utilized to protect or reduce the effect of the magnetic field on part or all of the interior cab of the vehicle, boat or airplane or any components contained therein, or to affect the magnetic field created to further the purpose(s) of the invention (which may include affecting the characteristics, distribution, focus or properties of the magnetic field).

When it is referred to herein that there may be a magnetic shield interposed between the one or more magnets and some other component, such as the interior cab of the vehicle, boat or airplane, or the components therein, the shield being interposed may be wholly or partially interposed within the scope of this invention.

This invention contemplates that a therapeutic wave source may also be positioned within or on the steering wheel, said therapeutic wave source directs therapeutic waves to a position at or above the steering wheel. Such therapeutic waves may include any form or type of waves or energy which currently or is later learned to have a therapeutic, healing, preventative, health or biological effect on the operator of the vehicle. This invention contemplates that later epidemiological studies or discoveries may made which have a therapeutic effect on the operator of the device, in the form of therapeutic waves or energy.

The term therapeutic is also used herein to cover and include any such wave or energy source which has a therapeutic, health care or biological effect on the operator of the vehicle, including a magnetic field, an electric field, infrared waves, or any others with a therapeutic or health care effect.

For example, it may later be determined that wave-forms or energy anywhere in the electromagnetic spectrum provide a therapeutic or health care effect to the operator. For example, if what are commonly known or referred to as laser light waves (which may be in the 630 to 670 nanometer wavelength range) are later found to be therapeutic to the hands or wrists of the vehicle operator, they may be placed on or in the steering wheel, to provide the therapeutic waves to the operator. The source of power to generate the laser for example may be by battery or conductor to the computer or another known source.

FIG. 1 illustrates a steering wheel 1 with a steering wheel body 2, a hub 5, and steering wheel body supports 6 which hold or attach the steering wheel body 2 to the hub 5. There are numerous known shapes, configurations, sizes and components for steering wheels in general, including for each of the applications contemplated by this invention, such as in vehicles, airplanes and boats.

FIG. 1 also illustrates a magnetic field 8 which has been created around the steering wheel 1. The depiction of the magnetic field 8 could also be of an electric field or some other field of therapeutic waves, within the contemplation of this invention.

Figure 2:
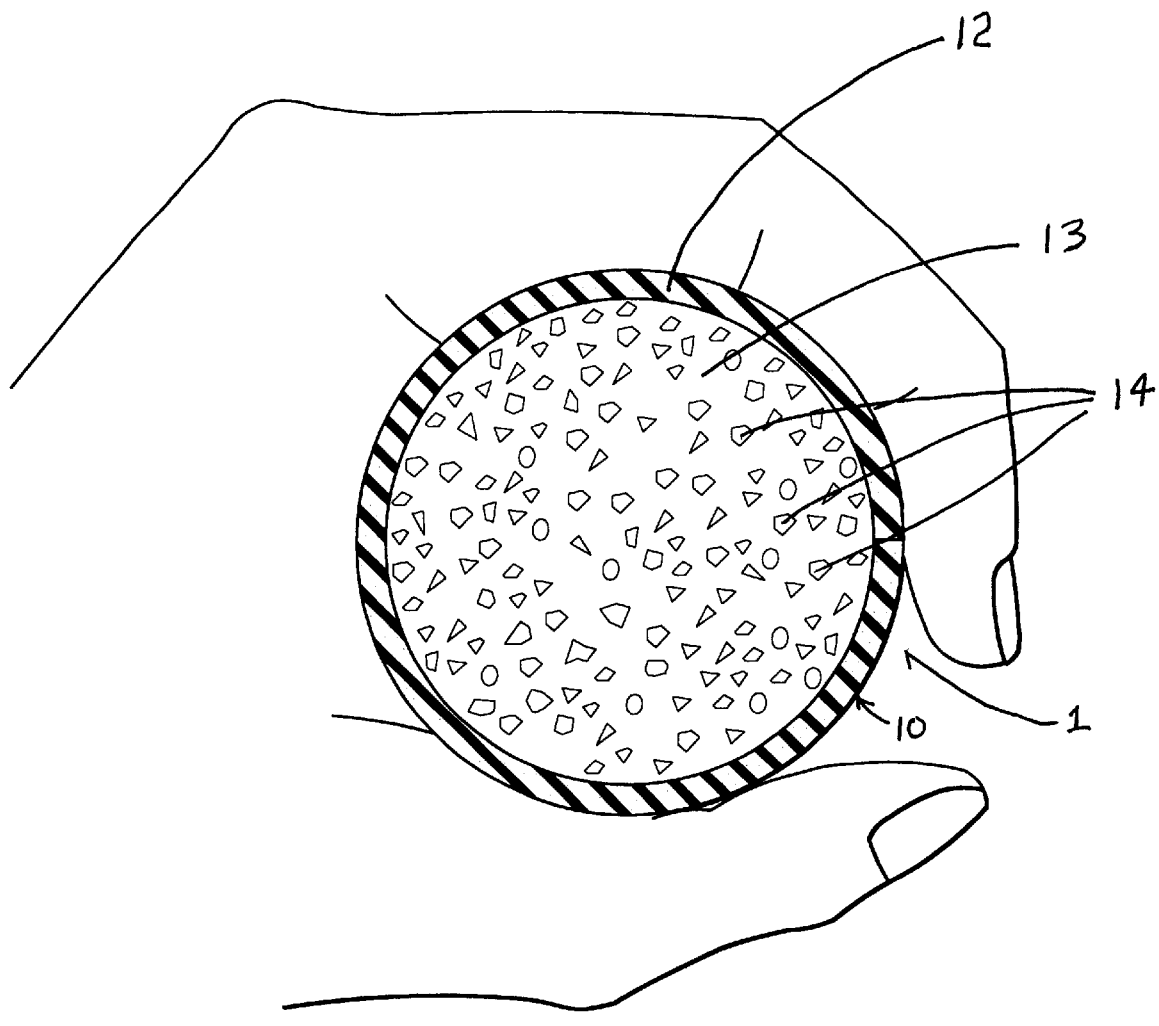
FIG. 2 is side section view of one potential embodiment of an ergonomic steering wheel contemplated by this invention, herein the inner portion of the steering wheel contains the magnetic particles.

FIG. 2 is a section view of a steering wheel 1 contemplated by this invention, wherein the body of the steering wheel contains the magnetized material which creates the magnetic field and/or electric field.

FIG. 2 illustrates a vehicle operator hand around a steering wheel 1. The steering wheel 1 includes an outer surface 10, an outer body portion 12 which is generally a radially outward side, a steering wheel body core 13, with distributed magnetized particles 14 contained therein. Although not depicted in FIG. 2, the steering wheel 1 is generating or creating a magnetic field and/or electric field (or other wave field) around the exterior of the steering wheel 1.

Each magnetized particle may be very small in size or may comprise a magnet of any size.

Figure 3:
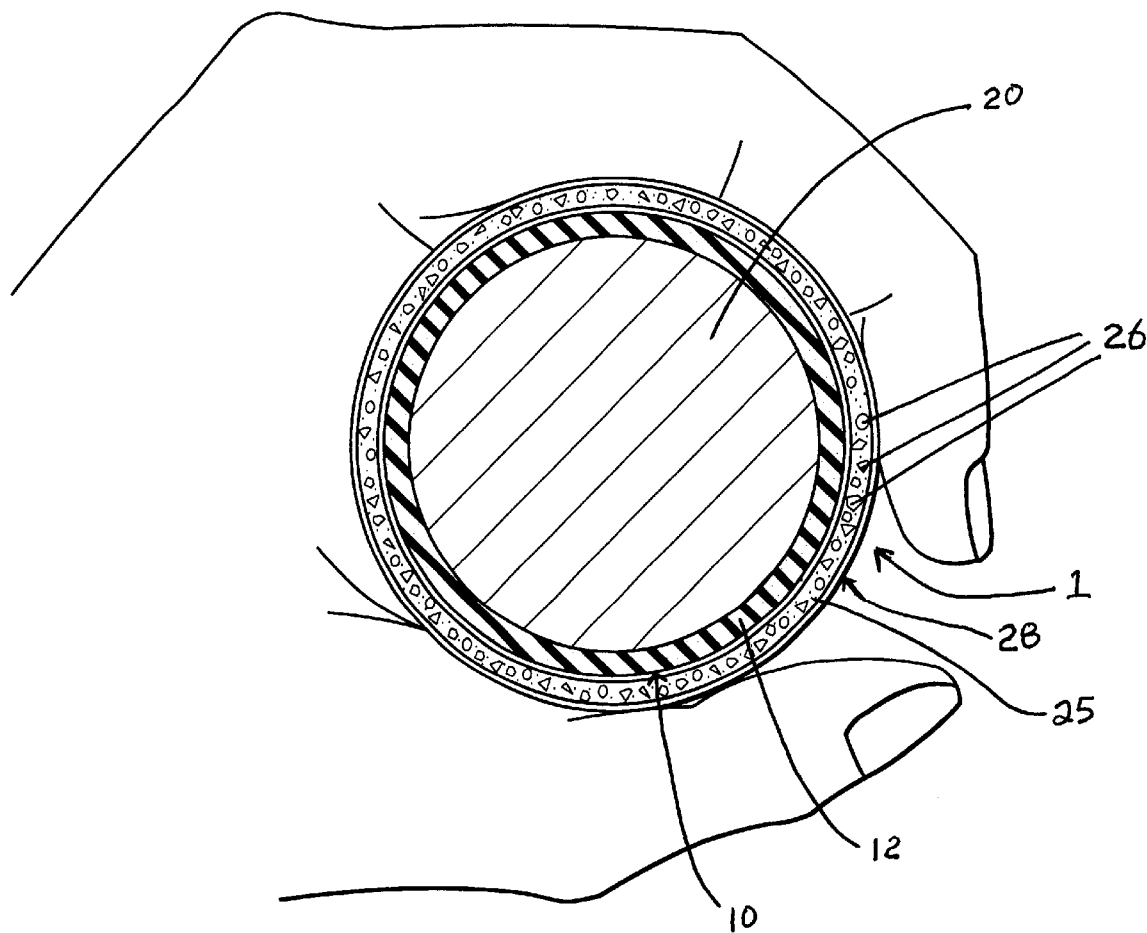
FIG. 3 is the same side section view as shown in FIG. 2, only of an alternative embodiment of a steering wheel as contemplated by this invention, wherein the wave field is generated by a steering wheel cover wrapped around a traditional steering wheel, the steering wheel cover generating or creating the magnetic, electric or other field around the steering wheel.

FIG. 3 is a section view of a steering wheel 1 contemplated by this invention, wherein an outer cover is utilized to create or generate the magnetic field and/or electric field around the steering wheel 1. Although not depicted in FIG. 3, the steering wheel 1 (via the cover) is generating or creating a magnetic field and/or electric field (or other wave field) around the exterior of the steering wheel 1.

It will be appreciated that the cover may be a partial or entire cover of the steering wheel as contemplated by this invention.

FIG. 3 illustrates a steering wheel body core 20, an outer steering wheel surface 10 and an outer body portion 12. Surrounding the outer steering wheel surface 10 is a steering wheel cover 25, the steering wheel cover 25 including distributed magnetized particles 26 therein. The steering wheel cover 25 is wrapped around or formed to or on the outer steering wheel surface 10, and includes an outer contact surface 28. The outer contact surface 28 is the contact location for the vehicle operator to contact and hold the steering wheel 1.

The steering wheel over 25 is particularly configured to cover or wrap around the particular steering wheel being covered or around which a magnetic field is desired.

The outer layer can be any type of material which is desirable for interfacing with the hands of the operator of the vehicle, boat or airplane, such as leather, synthetic materials, or any one of a number of other materials, all within the contemplation of this invention.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the Doctrine of Equivalents.

I claim:

1. A steering wheel for a vehicle, comprising:
    a. a magnetized steering wheel body which includes an outer steering wheel surface and wherein the magnetized steering wheel body creates a magnetic field around itself.

2. A steering wheel as recited in claim 1, and wherein the steering wheel body further creates an electric field around the steering wheel body.

3. A steering wheel as recited in claim 1, and wherein the polarity of the magnetized steering wheel body alternates between at least one north polarity and at least one south polarity.

4. A steering wheel for a vehicle, comprising:
    a. a steering wheel body which includes an outer steering wheel surface; and
    b. one or more magnets positioned within the steering wheel body, wherein said one or more magnets create a magnetic field around the outer steering wheel surface of the steering wheel body.

5. A steering wheel as recited in claim 4, and wherein the one or more magnetized particles further create an electric field around the steering wheel body.

6. A steering wheel as recited in claim 4, and wherein the polarity of the one or more magnetized particles alternates between at least one north polarity and at least one south polarity.

7. A steering wheel for a vehicle as recited in claim 4, and further wherein the one or more magnets define part or all of the outer steering wheel surface.

8. A steering wheel for a vehicle as recited in claim 4, and further wherein the one or more magnets are positioned at the outer steering wheel surface.

9. A steering wheel for a vehicle as recited in claim 4, and further wherein the one or more magnets are magnetized particles.

10. A steering wheel for a vehicle, comprising:
   a. a steering wheel body which includes an outer steering wheel surface; and
   b. a means for creating a non-specific magnetic field at least partially around the outer steering wheel surface.

11. A steering wheel for a vehicle as recited in claim 10, and further wherein the magnetic field created is wholly around the outer steering wheel surface.

12. A steering wheel for a vehicle as recited in claim 10, and further wherein the means for creating a magnetic field at least partially around the outer steering wheel surface is a flexible steering wheel cover with magnetized particles therein partially or wholly around the steering wheel body.

13. A steering wheel for a vehicle as recited in claim 10, and further wherein the means for creating a magnetic field at least partially around the outer steering wheel surface is with magnetized particles in the steering wheel body.

14. A steering wheel for a vehicle as recited in claim 11, and further wherein the means for creating a magnetic field at least partially around the outer steering wheel surface is with magnetized particles at the outer steering wheel surface.

15. A flexible steering wheel cover as recited in claim 14, and wherein the polarity of the one or more magnetized particles alternates between at least one north polarity and at least one south polarity.

16. A steering wheel as recited in claim 14, and wherein the one or more magnetized particles further create an electric field around the steering wheel body.

17. A flexible steering wheel cover for a vehicle comprising:
   a steering wheel cover body which is comprised of:
      an outer layer,
      an inner layer for contact with a steering wheel when the steering wheel cover is partially or wholly wrapped around the steering wheel; and
      one or more magnetized particles between the outer layer and the inner layer, the one or more magnetized particles creating a magnetic field around the steering wheel cover.

18. A flexible steering wheel cover as recited in claim 17, and wherein the polarity of the one or more magnetized particles alternate between at least one north polarity and at least one south polarity.

19. A flexible steering wheel cover as recited in claim 17, and further wherein the outer layer does not contain magnetized particles.

20. A flexible steering wheel cover for a vehicle comprising:
   a steering wheel cover body which is comprised of:
      an outer layer,
      an inner layer for contact with a steering wheel when the steering wheel cover is partially or wholly wrapped around the steering wheel; and
      one or more magnets between the outer layer and the inner layer, the one or more magnets creating a magnetic field around the steering wheel cover.

21. A flexible steering wheel cover as recited in claim 20, and further wherein the outer layer does not contain magnets.

22. A flexible steering wheel cover for a vehicle comprising:
   a steering wheel cover body which is comprised of:
      an outer layer,
      an inner layer configured to contact a steering wheel when the steering wheel cover is partially or wholly wrapped around the steering wheel; and
   wherein the steering wheel cover body includes a means for creating a magnetic field around the outer layer of the steering wheel cover.

23. A flexible steering wheel cover for a vehicle as recited in claim 22 and further wherein the means for creating a magnetic field around the outer layer of the steering wheel cover includes one or more magnets between the outer layer and the inner layer.

24. A flexible steering wheel cover for a vehicle as recited In claim 22, and further wherein the means for creating a magnetic field around the outer layer of the steering wheel cover includes one or more magnetized particles distributed in the steering wheel cover body.

* * * * *